United States Patent [19]

Reiner

[11] 4,260,613

[45] Apr. 7, 1981

[54] PYRIDOXINE DERIVATIVES

[75] Inventor: Alberto Reiner, Como, Italy

[73] Assignee: Crinos Industria Farmacobiologica S.p.A., Italy

[21] Appl. No.: 131,020

[22] Filed: Mar. 17, 1980

Related U.S. Application Data

[62] Division of Ser. No. 54,613, Jul. 3, 1979.

[30] Foreign Application Priority Data

Jul. 31, 1978 [IT] Italy ............................... 22637 A/78
May 23, 1979 [IT] Italy ............................... 22939 A/79

[51] Int. Cl.³ .................. A61K 31/44; A61K 31/435; C07D 213/30; C07D 491/056
[52] U.S. Cl. .................. 424/256; 424/263; 546/116; 546/301
[58] Field of Search ................ 546/290, 115, 116, 301

[56] References Cited

U.S. PATENT DOCUMENTS 3,285,924  11/1966  Osbond et al. ........................ 546/301

FOREIGN PATENT DOCUMENTS 709330  6/1966  Italy ............................... 546/116
42-9341  5/1967  Japan ............................. 546/116
42-9348  5/1967  Japan ............................. 546/116

OTHER PUBLICATIONS

Korytnyk et al., Chem. Abstracts, vol. 57, col. 5923, (1962).
Paul et al., Chem. Abstracts, vol. 70, abst. 96571f, (1979).
Chemical Abstracts, vol. 68, abstracts 68892b and 68893c, (1968), (absts. of Japanese Patents 42-9341 & 42-9348).
Chem. Abstracts, vol. 69, abst. 106,474x, (1968).
Chem. Abstracts, vol. 84, abst. 59209n, (1976).

*Primary Examiner*—John D. Randolph
*Attorney, Agent, or Firm*—Ostrolenk, Faber, Gerb & Soffen

[57] ABSTRACT

The invention concerns novel piridoxine derivatives of the general formula:

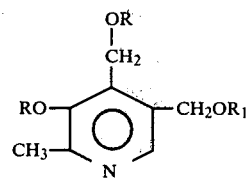

which show anti-inflammatory activity and moreover may show, although not necessarily, also analgesic and/or anti-pyretic activity.

9 Claims, No Drawings

PYRIDOXINE DERIVATIVES

This is a division of application Ser. No. 54,613, filed July 3, 1979.

The present invention concerns novel pyridoxine derivatives having anti-inflammatory activity.

The novel pyridoxine compounds of this invention are esters of pyridoxine and of the isopropylidene derivative thereof having the following general formula:

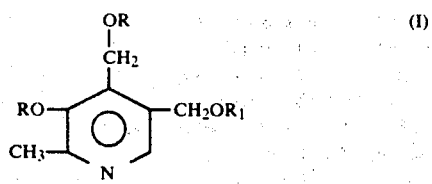

wherein each of the groups R represents a hydrogen atom or taken together represent an isopropylidene group and $R_1$ represents a moiety selected from the group consisting of 2-hydroxybenzoic acid, 2-[(2,3-dimethylphenyl)-amino]-benzoic acid, 4-allyloxy-3-chlorophenyl-acetic acid, 2-(3-benzoylphenyl)-propionic acid, 2-(4-isobutylphenyl)-propionic acid, d-2-(6-methoxy-2-naphtyl)-propionic acid, 2-[(3-(trifluoromethyl)-phenylamino]-benzoic acid or 2-[3-trifluoromethyl)-phenyl-amino]-nicotinic acid and their addition salts with inorganic and organic acids, physiologically acceptable at the doses at which the products of the present invention are administered.

Illustrative examples of organic and inorganic addition salts of the compounds of formula (I) comprise chlorhydrates, bromhydrates, sulphates, acetates, succinates, maleates, fumarates, tartrates, salicylates, cyclohexylsulphamates, nicotinates.

For the purpose of the present invention, the compounds of general formula (I) will be defined as "pyridoxine 5-ester" and "isopropylidenepyridoxine 5-ester" of the above-mentioned corresponding acids.

As referred above, the inventive compound of the instant invention show anti-inflammatory activity and moreover may show, although not necessarily, also analgesic and/or anti-pyretic activity. The anti-inflammatory activity of the novel compounds of the instant invention has been confirmed by means of the caraganin-edema test on the rat.

It is known that the above-mentioned free acids show anti-inflammatory activity, and it is also known that the said acids have also an ulceragenic activity which reduces manageability and which can limit their use. We have thought as an hypothesis that the ulcer-causing activity of these compounds could be due to their nature and in particular to the presence of a free carboxyl group. Therefore, by esterifying said free carboxyl group, it should be possible to eliminate, or at least to substantially reduce, the said ulcer-causing activity, maintaining, with an appropriate selection of the alcohol, the anti-inflammatory activity. For this purpose, pyridoxine has been selected both because it is a basic alcohol of very low toxicity, and because it seems to have a cellular eutrophyzing action which supposedly could further antagonize the ulceragenic properties of the starting acids.

In order to verify the validity of this hypothesis, particularly strict toxicological and pharmacological tests were carried out on some of the novel compounds of the instant invention, viz. the pyridoxine 5-ester of the 2-(4-isobutylphenyl)-propionic acid and the isopropylidenepyridoxine 5-ester of the 2-(4-isobutylphenyl)-propionic acid, in comparison with the corresponding free acid. The results of these tests are as follows.

TOXICITY

The acute toxicity has been determined by administering the substances per os in a sole dose to the mouse after 18 hours of fasting. The $LD_{50}$ has been determined according to Litchfield and Wilcoxon (J. Pharmacol. Exp. Ther. 96, 99, 1949).

The ulcer-causing activity has been determined by administering the substances per os to rats which have fasted 18 hours and evaluating the presence of gastric lesions 7 hours after the treatment. The $UD_{50}$ has been determined according to Litchfield and Wilcoxon (J. Pharmacol. Exp. Ther. 96, 99, 1949).

|  | $LD_{50}$ per os/mouse (mg/kg) | Ulcer-causing Activity $UD_{50}$ per os/rat (mg/kg) |
|---|---|---|
| 2-(4-isobutylphenyl)-propionic pyridoxine 5-ester | >2000 | 365 |
| 2-(4-isobutylphenyl)-propionic isopropylidene-pyridoxine 5-ester | >2200 | >400 |
| 2-(4-isobutylphenyl)-propionic acid | 800 (1) | 38 |

(1) Adams S.S. et al., Tox. Appl. Pharmacol., 15, 310, 1969

ANTI-INFLAMMATORY ACTIVITY

Caraganin-edema test according to Winter et al (Proc. Soc. Exp. Biol. Med., 111, 544, 1962) in the normal rat. The anti-inflammatory activity is expressed as a percentage of inhibition, after 3 and 6 hours, with respect to the controls.

ANALGESIC ACTIVITY

Test of Randall and Selitto (Arch.Ing.Pharmacodyn., 111, 409, 1957) on the rat. The analgesic activity is expressed as a percent variation from the algogenic stimulus, after 3 and 5 hours with respect to the controls.

|  | dose mg/kg per os | ANTI-INFLAMMATORY Inhibition % | | ANALGESIC ACTIVITY Variation % | |
|---|---|---|---|---|---|
|  |  | 3hrs | 5hrs | 3hrs | 5hrs |
| 2-(4-isobutylphenyl)-propionic pyridoxine 3-ester | 6.25 | 27.1 | 24.8 | — | — |
|  | 12.5 | 41.1 | 28.4 | +61.2 | +71.4 |
|  | 25 | 43.6 | 37.6 | — | — |
|  | 50 | 55.1 | 42. | +129.6 | +134.3 |
|  | 100 | — | — | — | — |
| 2-(4-isobutylphenyl)-propionic isoptopyliden-pyridoxine 5-ester | 6.25 | — | — | — | — |
|  | 12.5 | 19.6 | 18.3 | +77.5 | +39.0 |
|  | 25 | 13.1 | 12.8 | — | — |
|  | 50 | 43.9 | 39.4 | +122.5 | +78.1 |
|  | 100 | 60.7 | 42.2 | — | — |
| 2-(4-isobutylphenyl)-propionic acid | 6.25 | — | — | — | — |
|  | 12.5 | 33.6 | 16.5 | +86.7 | +83.8 |
|  | 25 | 43.9 | 19.3 | — | — |
|  | 50 | 54.2 | 26.6 | +146.9 | +69.5 |
|  | 100 | 49.5 | 32.1 | — | — |

The above-referred results confirm our hypothesis and clearly show the remarkable advantages of pyridoxine 5-ester and isopropylidene pyridoxine 5-ester of 2-(4-isobutylphenyl)-propionic acid with respect to the free acid, both for the lower toxicity and ulcer-causing activity and for the anti-inflammatory and analgesic activity. In fact, it is noted that the novel products of the instant invention besides having a much more favourable therapeutic index (toxicity vs. activity), and surprisingly show a much more prolonged activity. This property of the novel products of the invention is particularly important inasmuch as it allows a reduction of the daily doses of the drug, therefore, making its use still safer.

The novel compounds of the instant invention are essentially prepared by reacting isopropylidenepyridoxine of formula:

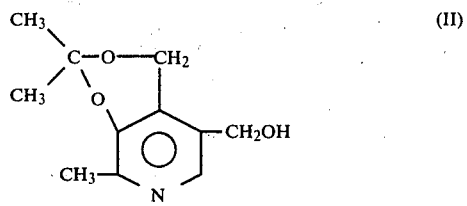

or a reactive derivative thereof, with a reactive derivative of an acid selected among the group consisting of 2-hydroxybenzoic acid, 2-[(2,3-dimethyl-phenyl)-amino]-benzoic acid, 4-allyloxy-3-chlorophenyl-acetic acid, 2-(3-benzoylphenyl)-propionic acid, 2-(4-isobutylphenyl)-propionic acid, d-2-(6-methoxy-2-naphthyl)-propionic acid, 2-[3-(trifluoromethyl)-phenylamino]-benzoic acid or 2-[3-trifluoromethyl)-phenylamino]-nicotinic acid, for esterification and, if desired, hydrolyzing the isopropylidene group with methods known per se.

According to a preferred embodiment of the instant invention, the esterification is carried out by reacting an isopropylidene pyridoxine of formula (II) with a halide of one of the above-listed acids in the presence of an acid-accepting agent to obtain the inventive compounds of formula (I) wherein the groups R, taken together, represent a isopropylidene group. Said compounds can then be hydrolyzed with an aqueous solution of a mineral acid thus yielding the corresponding compounds of formula (I) wherein each of the groups R represents a hydrogen atom.

The above-referred process can advantageously be carried out by using as an acid halide the corresponding chloride, and as an acid-accepting agent tertiary amines, such as, e.g. triethylamine, pyridine, dimethylaniline, operating at a temperature of from 10° C. to 60° C. Moreover, the reaction can advantageously be carried out in a non-reactive solvent, such as e.g. chloroform, carbon tetrachloride, benzine, or an excess of a tertiary amine.

The acid hydrolysis is preferably carried out in 1-10% hydroalcoholic solutions of hydrochloric or sulphuric acid at a temperature of from 25° C. to 100° C.

The inventive compound of formula (I) wherein the groups R represent an isopropylidene group are preferably isolated from the reaction mixture in the form of their salts, advantageously as hydrochlorides and can then be purified by crystallizing from a suitable solvent, such as e.g. acetone, methanol, ethanol. The said salts are white solids normally water-soluble, to a different extent, according to the acid used for salt formation.

The inventive compounds of formula (I) wherein the groups R represent a hydrogen atom, are preferably isolated from the reaction mixture in the form of the free base and can be purified by crystallization from a suitable solvent, such as e.g. ethanol or methanol. Said compounds are white water-insoluble solids. They can be easily transformed in the corresponding addition salts by treating them with an equivalent amount of the desired acid dissolved in an organic solvent, such as e.g., ethanol, acetone, ethylmethylketone, methylisobutylketone.

Said salts appear as white solids, water-soluble, to a different extent according to the acid used for salt formation.

According to another procedure, the inventive compounds of formula (I) may be prepared by transesterification by reacting the isopropylidenepyridoxine of formula (II) with a lower alkyl ester of 2-hydroxybenzoic acid, 2-[(2,3-dimethylphenyl)-amino]-benzoic acid, 4-allyloxy-3-chlorophenylacetic acid, 2-(3-benzoylphenyl)-propionic acid, 2-(4-isobutylphenyl)-propionic acid, d-2-(6-methoxy-2-naphthyl)-propionic acid, 2-[3-(trifluoromethyl)-phenylamino]-benzoic acid or 2-[3-(trifluoromethyl)-phenylamino]-nicotinic acid to give the compounds of formula (I) in which the R groups taken together represent an isopropylidene group. These may be hydrolized subsequently as above specified to give the corresponding compounds of formula (I) in which both R groups represent a hydrogen atom. This second method is to be preferred to the esterification through acid chloride above mentioned in case of acids having in their molecule an amine group, such as 2-[3-(trifluoromethyl)-phenylamino]-benzoic acid or 2-[3-(trifluoromethyl)phenylamino]-nicotinic acid.

The transesterification is effected employing preferably the methyl or ethyl ester, advantageously the methyl ester, by conducting the reaction in an inert solvent, such as e.g., benzene, toluene or xylene at a temperature of from 50° C. to the reflux temperature of the reaction mass. Further, the reaction is preferably carried out in the presence of an alkaline catalyst, such as e.g. sodium methylate or ethylate.

The starting products as used for preparing the inventive compounds of formula (I) are obtained by various known methods, for example: the chlorides of the acids: from the corresponding acids and thionyl chloride; the alkyl esters: from the chloride of the corresponding acid and either methyl or ethyl alcohol; the isopropylidenepyridoxine: according to the method of Korytuyk and Wiedeman (J.Chem.Soc., (1962), 2531).

This invention further relates to pharmaceutical compositions comprising, as the active substance, at least one of the compounds of formula (I) as above defined, in combinations with a carrier or a pharmaceutical vehicle, and formulated either for oral, parenteral, rectal administration or for topical application. Compositions for oral administration may be in solid or liquid form. The solid compositions comprise, for example, capsules, tablets, sugar-coated pills for which carriers may be used such as e.g. lactose, starch, talc, magnesium stearate. Oral compositions in the liquid form comprise, for example, syrups, drops, elixirs, suspensions for which proper liquid vehicles may be used, comprising water and sweetening, aromatizing, dispersing and/or other agents.

Compositions for parenteral administration consist preferably of either aqueous injectable solutions—comprising water glycol mixtures—or oily injectable solutions, for example, olive or peanut oil solutions.

For the preparation of solutions, both for oral and parenteral use, the compounds of this invention are preferably used as soluble, non-toxic, acid addition salts.

Finally, for rectal and topic preparations, conventional bases for suppositories are used and, respectively, for salves and creams.

The pharmaceutical compositions of this invention are preferably formulated so as to allow administration of a unit dose of active substance, for example, capsules, tablets, sugar-coated pills, phials and suppositories.

As a unit dose, one which is commensurate with the level of activity for the inventive compounds and to the desired effect is selected.

Suitably, the unit doses of active substance for oral and parenteral administration may be from 0.01 to 1 g, preferably from 0.025 to 0.700 g, those for rectal administration from 0.02 to 1.5 g, preferably from 0.05 to 1 g.

For topical application, the compounds of this invention may be formulated, for example, as dermatological creams, salves or solutions containing the active substance at weight-concentrations of 1–10%, preferably of 5%.

The following examples are merely illustrative of the invention and do not have any limiting character.

EXAMPLE 1

(a) 50 g of 2-(4-isobutyl-phenyl)-propionic acid are added portionwise to a solution of 25 ml of thionyl chloride in 60 ml of chloroform (the reaction is endothermic). The reaction mixture is taken slowly to reflux by adjusting the heating so that the gas evolution does not become violent, and then it is kept at reflux for 1 hour.

The solvent and the excess of thionyl chloride are removed under reduced pressure, to give an oily residue consisting of crude 2-(4-isobutylphenyl)-propionic acid, which may be used as such in the next step.

(b) 43 ml of triethylamine and 30.3 g. of isopropylidenepyridoxine are added, separately but contemporaneously, to a solution of 50 g of crude (2-(4-isobutyl-phenyl)-propionic acid chloride in 200 ml of chloroform, while stirring and cooling so that the temperature does not exceed 20° C. The reaction mass is kept under stirring at room temperature 2 hours, and then at 40°–45° C. for further 2 hours. After cooling, 200 ml of water are added and the chloroform layer is separated, thoroughly washed with water, dried over sodium sulphate and evaporated to dryness.

The oily residue is taken up with an 1:1 (v/v) acetone/cyclohexane blend and treated with gaseous hydrochloric acid. The crude hydrochloride of 2-(4-isobutyl-phenyl)-propionic isopropylidenepyridoxine 5-ester which, after washing by trituration with 5% aqueous hydrochloric acid and drying, is crystallized from acetone (m.p. 189°–191° C.).

For $C_{24}H_{31}NO_4Cl$; calc.% C 66.42 H 7.43 N. 3.23; found % C 65.90 H 7.64 N. 3.07.

By proceeding in a substantially similar way one further obtained:

2-hydroxybenzoic isopropylidenepyridoxine 5-ester hydrochloride (m.p. 149°–152° C.)

For $C_{18}H_{20}NO_5Cl$; calc.% C 59.1 H 5.51 N 3.83; found % C 59.19 H 5.42 N 3.86.

2-(3-benzoylphenyl)-propionic isopropylidenepyridoxine 5-ester hydrochloride (m.p. 144°–145° C.)

For $C_{27}H_{28}NO_5Cl$; calc.% C 67.28 H 5.85 N 2.9; found % C 67.75 H 5.61 N 3.1.

EXAMPLE 2

55 g of methyl ester of (4-allyloxy-3-chloro-phenyl)-acetic acid, 40 g of isopropylidenepyridoxine, 3.5 g of sodium methylate in 500 ml of anhydrous toluene, are reflux heated, distilling off the methanol which forms during the reaction. When no more methanol forms, one still heats for 1 hour at 80°–90° C., and then the solvent is removed under reduced pressure. Before the reaction mass wholly solidifies, it is dissolved again in toluene, water is added and the mixture is filtered. The toluene solution is washed 2 additional times with water, and finally ether is added thereto so as to separate the unreacted isopropylidenepyridoxine, which precipitates. After filtering, the solvent is removed under reduced pressure and the oily residue, upon being taken up with methylisobutylketone, is treated with gaseous hydrochloric acid. (4-allyloxy-3-chloro-phenyl)-acetic isopropilidenepyridoxine 5-ester hydrochloride precipitates, which is crystallized from acetone (m.p. 177°–178° C.).

For $C_{22}H_{25}NO_5Cl_2$; calc.% C 58.16 H 5.55 N 3.08; found % C 58.02 H. 5.74 N 3.15.

By proceeding in a substantially similar way, one further obtained:

[2-(2,3-dimethylphenyl)-amino]-benzoic isopropylidenepyridoxine 5-ester hydrochloride (m.p. 195°–198° C.).

for $C_{26}H_{29}N_2O_4Cl$; cal.% C 66.59 H 6.23 N 5.97; found % C 66.72 H 6.38 N 5.91.

By proceeding as above described and using equivalent amounts of fumaric acid (in a methyl isobutylketone solution) instead of hydrochloric acid, one further obtained:

d-2-(6-methoxy-2-naphthyl)-propionic isopropylidene 5-ester neutral fumarate (m.p. 148°–149° C.)

For $C_{54}H_{58}N_2O_{14}$; calc.% C 67.63 H 6.01 N 2.92; found % C 68.02 H 5.89 N 2.89.

EXAMPLE 3–8

A mixture of 50 g. of 2-(4-isobutyl-phenyl)-propionic isopropylidenepyridoxine 5-ester hydrochloride, 5 ml of concentrated hydrochloric acid, 150 ml of ethanol and 500 ml of water are heated to slow reflux during ½ hour. The mixture is cooled, filtered on carbon and the solution is treated with diluted aqueous ammonia. 2-(4-isobutyl-phenyl)-propionic pyridoxine 5-ester precipitates, which is filtered, thoroughly washed and finally crystallized from ethanol (m.p. 153°–157° C.).

For $C_{21}H_{27}NO_4$; calc.% C 70.56 H 7.61 N 3.92; found % C 70.26 H 7.70 N 3.56.

By proceeding as above described, one further obtained:

[2-(2,3-dimethyl-phenyl)-amino]-benzoic pyridoxine 5-ester (m.p. 215°–216° C.).

For $C_{23}H_{24}N_2O_4$; calc. % C 70.389 H 6.164 N 7.138; found % C 70.18 H 6.20 N 7.24. d-2-(6-methoxy-2-naphthyl)-propionic pyridoxine 5-ester (m.p. 155°–156° C.)

For $C_{22}H_{23}NO_5$; calc. % C 69.28 H 6.1 N 2.92; found % C 70.1 H 5.98 N 2.95.

salicylic pyridoxine 5-ester m.p. 174°–176° C.)

For $C_{15}H_{15}NO_5$; calc. % C 62.28 H 5.23 N 4.84; found % C 62.94 H 5.21 N 4.78.

(4-allyloxy-3-chloro-phenyl)-acetic pyridoxine 5-ester (m.p. 145° C.)

For $C_{19}H_{20}NO_5Cl$; calc.% C 60.39 H 5.33 N 3.70; found % C 60.18 H 5.42 N 3.68.

2-(3-benzoyl-phenyl)-propionic pyridoxine 5-ester (m.p. 122°–124° C.)

For $C_{24}H_{23}NO_5$; calc.% C 71.09 H 5.71 N 3.45; found % C 71.12 H 5.65 N 3.40.

EXAMPLE 9

10 g of [2-(2,3-dimethyl-phenyl)-amino]-benzoic isopropylidenepyridoxine 5-ester hydrochloride, dissolved into 50 ml of water are treated dropwise with 10% $NH_4OH$ until pH 7.5-8. The solid which precipitates is filtered, thoroughly washed with water and dried obtain [2-(2,3-dimethyl-phenyl) amino]-benzoic isopropylidenepyridoxine 5-ester (m.p. 165°–167° C.).

EXAMPLES 10–21

35 g of 2-(4-isobutyl-phenyl)-propionic pyridoxine 5-ester dissolved into 80 ml. of methylisobutylketone are treated with 14 g of salicylic acid dissolved into 40 ml of methylisobutylketone, to give the corresponding addition salt (m.p. 110°–113° C.).

The reaction may be effected also using ethanol as a solvent. Likewise one obtains:

2-(4-isobutyl-phenyl)-propionic pyridoxine 5-ester nicotinate (m.p. 142°–143° C.)

2-(3-benzoyl-phenyl)-propionic pyridoxine 5-ester nicotinate (m.p. 112°–114° C.)

2-(3-benzoyl-phenyl)-propionic pyridoxine 5-ester hydrochloride (m.p. 158°–164° C.)

(4-allyloxy-3-chloro-phenyl)-acetic pyridoxine 5-ester nicotinate (m.p. 136°–138° C.)

(4-allyloxy-3-chloro-phenyl)-acetic pyridoxine 5-ester 2-hydroxybenzoate (m.p. 143°–144° C.).

(4-allyloxy-3-chloro-phenyl)-acetic pyridoxine 5-ester hydrochloride (m.p. 201°–202° C.

2-hydroxy-benzoate pyridoxine 5-ester hydrochloride (m.p. 186°–188° C.).

d-2(6-methoxy-2-naphthyl)-propionic pyridoxine 5-ester nicotinate (m.p. 150°–151° C.)

d-2(6-methoxy-2-naphthyl)-propionic pyridoxine 5-ester neutral fumarate (m.p. 158°–159° C.)

[2-(2,3-dimethyl-phenyl)-amino]-benzoic pyridoxine 5-ester sulphate (m.p. 164°–166° C.)

[2-(2,3-dimethyl-phenyl)-amino]-benzoic pyridoxine 5-ester-hydrochloride (m.p. 126°–127° C.)

EXAMPLE 22

40 g. of the methyl ester of 2-[3-(trifluoromethyl)-phenylamino]-nicotinic acid, 20 g. of isopropylidenepyridoxine, 2 g. of sodium methylate in 1,000 ml of anhydrous toluene are heated distilling off the methanol which forms again during the reaction. At the end, the solvent is distilled off (finally under vacuum), thereby obtaining an oily residue which is dissolved again into chloroform and thoroughly washed with water. The chloroform solution is dried over sodium sulphate, treated with gaseous HCl and concentrated to small volume. Upon cooling, 2-[3-(trifluoromethyl)-phenylamino] nicotinic isipropylidenepyridoxine 5-ester hydrochloride separates, which, upon crystallizing from an ethanol/methanol mixture, has m.p. 180°–183° C. The product which has been obtained is triturated with little aqueous ethanol, treated with aqueous ammonia to a markedly alkaline pH, then it is filtered and crystallized from ethanol. 2-[3-(trifluoromethyl)phenylamino] nicotinic isopropylidenepyridoxine 5-ester base, m.p. 128°–130° C., is so obtained.

For $C_{24}H_{22}F_3N_3O_4$; calc.% N 8.87; found % 8.92.

EXAMPLE 23

40 g. of methyl ester of 2-[3-(trifluoromethyl) phenylamino] benzoic acid, 20 g. of isopropylidenepyridoxine, 2 g. of sodium methylate in 600 ml of a toluene/heptane mixture are reacted as described in the foregoing example. The obtained chloroform solution, upon washing with water and drying on sodium sulphate, is treated with gaseous HCl and filtered to eliminate any precipitate, thereafter removing the solvent. The residue is taken up with acetone/cyclohexane/ether from which 2-[-3-(trifluoromethyl)phenylamino]-benzoic isopropylidenepyridoxine 5-ester hydrochloride crystallized, which, upon crystallization from ethanol, has m.p. 180°–183° C. Then one proceeds as in Example 22, obtaining the 2-[3-(trifluoromethyl) phenylamino]benzoic isopropylidenepyridoxine 5-ester base, m.p. 81°–85° C.

For $C_{25}H_{23}N_2O_4F_3$; calc. % N 5.93; found % 5.84.

EXAMPLES 24–25

27 g. of 2-[3-(trifluoromethyl)phenylamino]nicotinic isopropylidenepyridoxine 5-ester, 300 ml of ethanol and 300 ml of 3% HCl are heated on boiling water-bath during 20 minutes. The mixture is kept for 2 hours at room temperature, aqueous ammonia is added, letting pH remain acid, and diluted with water. 2-[3-(trifluoromethyl)-phenylamino]-nicotinic pyridoxine 5-ester hydrochloride, m.p. 189°–191° C.

The product obtained is triturated with little aqueous ethanol, treated with aqueous ammonia to a markedly alkaline pH, filtered and crystallized from chloroform-ethanol. 2-[3-(trifluoromethyl)phenylamino]-nicotinic pyridoxine 5-ester base, m.p. 205°–206° C., is so obtained.

For $C_{21}H_{18}F_3N_3O_4$; calc.% N 9.7; found % 9.83.

By proceeding in a substantially analogous way, one also obtained:

2-[3-(trifluoromethyl)-phenylamino]benzoic pyridoxine 5-ester, m.p. 184°–188° C. (hydrochloride, m.p. 151°–153° C.).

For $C_{22}H_{19}F_3N_2O_4$; calc. % N 6.48; found % 6.39.

I claim:

1. Pyridoxine derivative of the formula

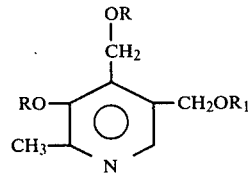

(I)

wherein
each of the R groups represents a hydrogen atom or taken together represent an isopropylidene group and $R_1$ represents a moiety selected from the group consisting of
2-[(2,3-dimethylphenyl)-amino]-benzoic acid, 2-(3-benzoylphenyl)-propionic acid, d-2-(6-methoxy-2-naphthyl)-propionic acid, 2-[3-(trifluoromethyl)-phenylamino]-benzoic acid or 2-[3-trifluoromethyl)-phenylamino]-nicotinic acid and their addition salts with inorganic and organic, physiologically acceptable, acids.

2. Derivative of formula (I), according to claim 1, wherein each of the R groups represents a hydrogen atom.

3. Derivative of formula (I), according to Claim 1, wherein the R groups, taken together, represent an isopropylidene group.

4. Derivative of formula (I), according to claim 1, in the form of hydrochlorides, hydrobromides, sulphates, acetates, succinates, maleates, salicylates, cyclohexylsulphamates, or nicotinates.

5. Anti-inflammatory composition for oral, parenteral, rectal administration or for topical application, characterized in that it contains an anti-inflammatory effective amount of at least one derivative of formula (I) according to claim 1, or a physiologically acceptable acid addition salt thereof, combined with conventional pharmaceutical carriers, vehicles, additives, fillers and/or stabilizers.

6. A process for preparing the pharmaceutical composition of claim 5, characterized by taking to a pharmaceutically suitable administration form at least one compound of general formula (I) according to claim 1, or a physiologically acceptable acid addition salt thereof, combined with conventional pharmaceutical carriers, vehicles, additives, fillers and/or stabilizers.

7. A method for treating inflammation, characterized by administrating to the patient by oral, parenteral, rectal or topical way an anti-inflammatory effective amount of a composition according to claim 5.

8. Derivative of formula (I) according to claim 2, wherein $R_1$ is a 2-[3-trifluoromethyl-phenylamino]-nicotinic group and the physiologically acceptable acid addition salts thereof.

9. Derivative of formula (I) according to claim 3, wherein $R_1$ is a 2-[3-trifluoromethyl-phenylamino]-nicotinic group and the physiologically acceptable acid addition salts thereof.

* * * * *